United States Patent
Rivest (10) Patent No.: US 10,539,257 B2
(45) Date of Patent: Jan. 21, 2020

(54) FITTING FOR MEDICAL PIPING SYSTEM

(71) Applicant: Omega Flex, Inc., Middletown, CT (US)

(72) Inventor: Dean W. Rivest, Oxford, PA (US)

(73) Assignee: OMEGA FLEX INC., Middletown, CT (US)

( * ) Notice: Subject to any disclaimer, the term of this patent is extended or adjusted under 35 U.S.C. 154(b) by 0 days.

(21) Appl. No.: 15/417,440

(22) Filed: Jan. 27, 2017

(65) Prior Publication Data

US 2018/0216762 A1 Aug. 2, 2018

(51) Int. Cl.
| | |
|---|---|
| *F16L 25/00* | (2006.01) |
| *F16L 33/26* | (2006.01) |
| *F16L 19/00* | (2006.01) |
| *F16L 19/02* | (2006.01) |
| *A61M 39/12* | (2006.01) |

(52) U.S. Cl.
CPC ......... *F16L 25/0054* (2013.01); *F16L 19/005* (2013.01); *F16L 19/0206* (2013.01); *F16L 33/26* (2013.01); *A61M 39/12* (2013.01)

(58) Field of Classification Search
CPC ....... F16L 13/14; F16L 13/141; F16L 13/146; F16L 13/142; F16L 13/161; F16L 13/165; F16L 2013/145; F16L 25/0036; F16L 25/0054
USPC ................ 285/382.7, 382, 382.1, 382.2, 343
See application file for complete search history.

(56) References Cited

U.S. PATENT DOCUMENTS

| | | | | |
|---|---|---|---|---|
| 3,528,689 | A * | 9/1970 | Roe | F16L 13/146 |
| | | | | 285/382.2 |
| 3,833,984 | A * | 9/1974 | Dietzel | B21D 39/04 |
| | | | | 29/523 |
| 4,251,094 | A * | 2/1981 | Pinto | F16L 13/147 |
| | | | | 285/382.5 |
| 4,842,310 | A * | 6/1989 | Muffke | B60T 17/04 |
| | | | | 285/334.5 |
| 5,088,771 | A * | 2/1992 | Hosseinian | B25B 27/10 |
| | | | | 285/382.2 |
| 5,346,262 | A * | 9/1994 | Liebig | F16L 13/146 |
| | | | | 285/23 |
| 5,799,989 | A | 9/1998 | Albino | |
| 5,921,591 | A | 7/1999 | Argent | |
| 9,800,040 | B2 * | 10/2017 | Rivest | H02G 3/0468 |
| 2002/0117226 | A1 | 8/2002 | Malcarne, Jr. | |
| 2005/0285401 | A1 * | 12/2005 | Treichel | F16L 19/065 |
| | | | | 285/382 |
| 2007/0273149 | A1 | 11/2007 | Duquette et al. | |
| 2008/0036207 | A1 | 2/2008 | Choi | |

(Continued)

OTHER PUBLICATIONS

International Search Report and Written Opinion for application PCT/US18/14160, dated May 23, 2018, 12 pages.

*Primary Examiner* — Aaron M Dunwoody
(74) *Attorney, Agent, or Firm* — Cantor Colburn LLP (57) ABSTRACT

A fitting for use with metal, corrugated tubing having peaks and valleys, the fitting includes a nut configured to receive the tubing; a sealing member for placement in a valley of the tubing, the sealing member including a sealing surface; and an adaptor configured to be press fit into the nut, the adaptor including an adaptor sealing surface; wherein upon assembly, the adaptor is press fit into the nut and the tubing is compressed between the adaptor sealing surface and the sealing surface.

13 Claims, 6 Drawing Sheets

(56) References Cited

U.S. PATENT DOCUMENTS

| | | | |
|---|---|---|---|
| 2010/0007140 A1* | 1/2010 | Duquette | F16L 13/142 |
| | | | 285/286.2 |
| 2011/0215570 A1* | 9/2011 | Treichel | F16L 23/0283 |
| | | | 285/334.5 |
| 2013/0087381 A1* | 4/2013 | Daughtry | H02G 3/0691 |
| | | | 174/660 |
| 2014/0306448 A1* | 10/2014 | Rivest | G01M 3/283 |
| | | | 285/354 |
| 2016/0123506 A1* | 5/2016 | Strunk | F16L 25/0036 |
| | | | 285/355 |
| 2017/0159858 A1* | 6/2017 | Strunk | F16L 25/0054 |
| 2018/0003322 A1* | 1/2018 | Treichel | F16L 19/0212 |
| 2018/0187803 A1* | 7/2018 | Strunk | B32B 1/00 |
| 2018/0224032 A1* | 8/2018 | Cole | F16L 25/0036 |

\* cited by examiner

FITTING FOR MEDICAL PIPING SYSTEM

BACKGROUND

Embodiments relate generally to fittings for use with piping, and more particularly, to fittings suitable for use with medical piping in health care facilities. Medical piping within health care facilities was traditionally rigid, copper tubing meeting NPFA 99 health care facilities code. The health care facilities encompass a wide variety of facilities, including hospitals, ambulatory health care centers and clinics, medical and dental offices, nursing homes, limited care facilities, etc. Traditionally, health care facilities used brazed copper tubing, this is supplied in short lengths and coupled together via brazing; any change in direction additionally required brazed joints. Installation of rigid, copper tubing is labor intensive and requires that each section of copper tubing be contained in a sealed, vented area so that the brazing process does not introduce contaminants to the surrounding area. The set-up and break down of the sealed, vented areas is time consuming and increases installation time.

SUMMARY

According to one embodiment, a fitting for use with metal, corrugated tubing having peaks and valleys includes a nut configured to receive the tubing; a sealing member for placement in a valley of the tubing, the sealing member including a sealing surface; and an adaptor configured to be press fit into the nut, the adaptor including an adaptor sealing surface; wherein upon assembly, the adaptor is press fit into the nut and the tubing is compressed between the adaptor sealing surface and the sealing surface.

In addition to one or more of the features described above, or as an alternative, further embodiments may include wherein the adaptor sealing surface is arcuate.

In addition to one or more of the features described above, or as an alternative, further embodiments may include wherein the adaptor sealing surface is spherical or toroidal.

In addition to one or more of the features described above, or as an alternative, further embodiments may include wherein the sealing surface is flat.

In addition to one or more of the features described above, or as an alternative, further embodiments may include wherein the sealing surface is frusto-conical.

In addition to one or more of the features described above, or as an alternative, further embodiments may include wherein the nut includes a first cavity configured to receive the adaptor; the adaptor including a sealing ridge formed thereon, the sealing ridge having an outer diameter greater than an inner diameter of the first cavity.

In addition to one or more of the features described above, or as an alternative, further embodiments may include wherein the nut includes a first cavity configured to receive the adaptor; the adaptor including a locking ridge formed thereon, the locking ridge having an outer diameter greater than an inner diameter of the first cavity.

In addition to one or more of the features described above, or as an alternative, further embodiments may include wherein the locking ridge includes an edge that mechanically fixes the nut on adaptor.

In addition to one or more of the features described above, or as an alternative, further embodiments may include wherein the adapter includes a locking ridge formed thereon and spaced from the sealing ridge, the locking ridge having an outer diameter greater than the outer diameter of the sealing ridge.

In addition to one or more of the features described above, or as an alternative, further embodiments may include wherein the locking ridge includes an edge that mechanically fixes the nut on adaptor.

In addition to one or more of the features described above, or as an alternative, further embodiments may include wherein the adaptor includes an engagement surface located between the sealing ridge and the locking ridge, the engagement surface having an outer diameter greater than the inner diameter of the first cavity.

In addition to one or more of the features described above, or as an alternative, further embodiments may include wherein the nut includes a second cavity; and the tubing includes a jacket; the fitting further comprising: a jacket lock ring configured for placement in the second cavity, the jacket lock ring including an outer surface including a tapered ramp and an inner surface including at least one ridge configured to engage the jacket; a swage sleeve configured for placement in the second cavity, the swage sleeve including a tapered surface facing the ramp on the jacket lock ring.

In addition to one or more of the features described above, or as an alternative, further embodiments may include wherein upon assembly, the swage sleeve is press fit into the second cavity and the tapered surface of the swage sleeve engages the ramp of the jacket lock ring to drive the jacket lock ring towards the jacket.

In another embodiment, a fitting for use with metal, corrugated tubing having peaks and valleys encased in a jacket, the fitting including: a nut including a first cavity and a second cavity and a shoulder extending radially inwardly between the first cavity and the second cavity, configured to receive the tubing through the second cavity; a sealing member configured for placement in a valley of the tubing, the sealing member including a sealing surface and a circumferential notch, the notch configured to abut against and receive the shoulder to limit movement of the sealing member; an adaptor configured to be press fit into the nut, the adaptor including an adaptor sealing surface, the adaptor including a sealing ridge formed thereon, the sealing ridge having an outer diameter greater than an inner diameter of the first cavity; a jacket lock ring configured for placement in the second cavity, the jacket lock ring including an outer surface including a tapered ramp and an inner surface including at least one ridge configured to engage the jacket; a swage sleeve configured for placement in the second cavity, the swage sleeve including a tapered surface facing the ramp on the jacket lock ring; wherein upon assembly, the adaptor is press fit into the first cavity and the swage sleeve is press fit into the second cavity, the tubing being compressed between the adaptor sealing surface and the sealing surface and the tapered surface of the swage sleeve engages the ramp of the jacket lock ring to drive the jacket lock ring towards the jacket.

DETAILED DESCRIPTION

Figure 1:
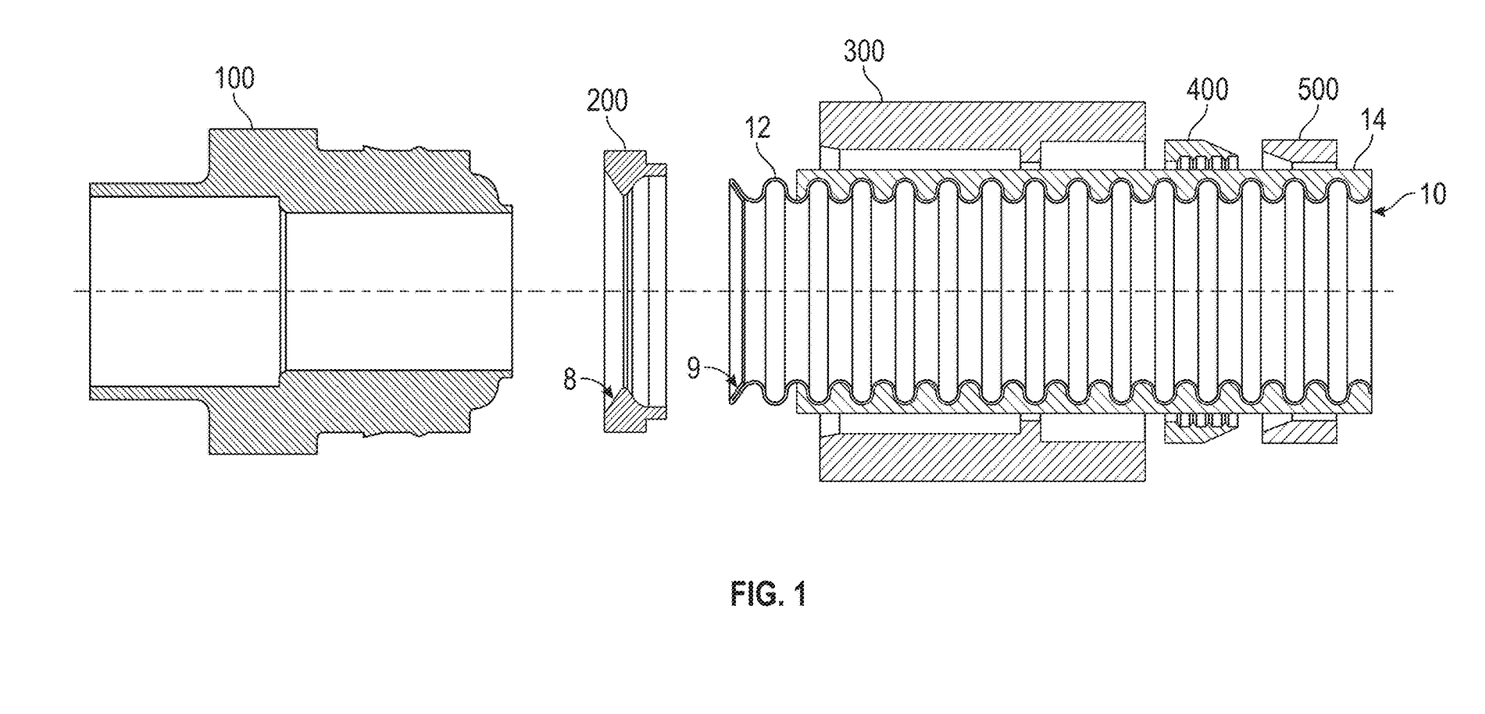
FIG. 1 is an exploded, cross-sectional view of a fitting and piping in an example embodiment.

FIG. 1 is an exploded, cross-sectional view of a fitting and flexible piping in an example embodiment. The piping 10 includes flexible, annular-corrugated, metal tubing 12 (e.g., copper alloy, stainless steel, etc.) and a jacket 14 having a smooth exterior. The jacket 14 may be a coextruded, non-metallic jacket which fills the spaces between the corrugations (e.g., peaks and valleys), thereby mechanically attaching the jacket 14 to the corrugated metal tubing 12. In one embodiment, the jacket 14 is a polymeric jacket such as low-density polyethylene. Other materials that offer sufficient tensile strength to resist corrugation movement under pressure could be utilized. Jacket 14 may include one or more fire retardant additives. The jacket 14 may meet ASTM E84, with maximum Flame Spread index of 25 and maximum Smoke Density Index of 50. The piping 10 may be implemented using MEDITRAC® metal piping for medical applications.

Figure 9:
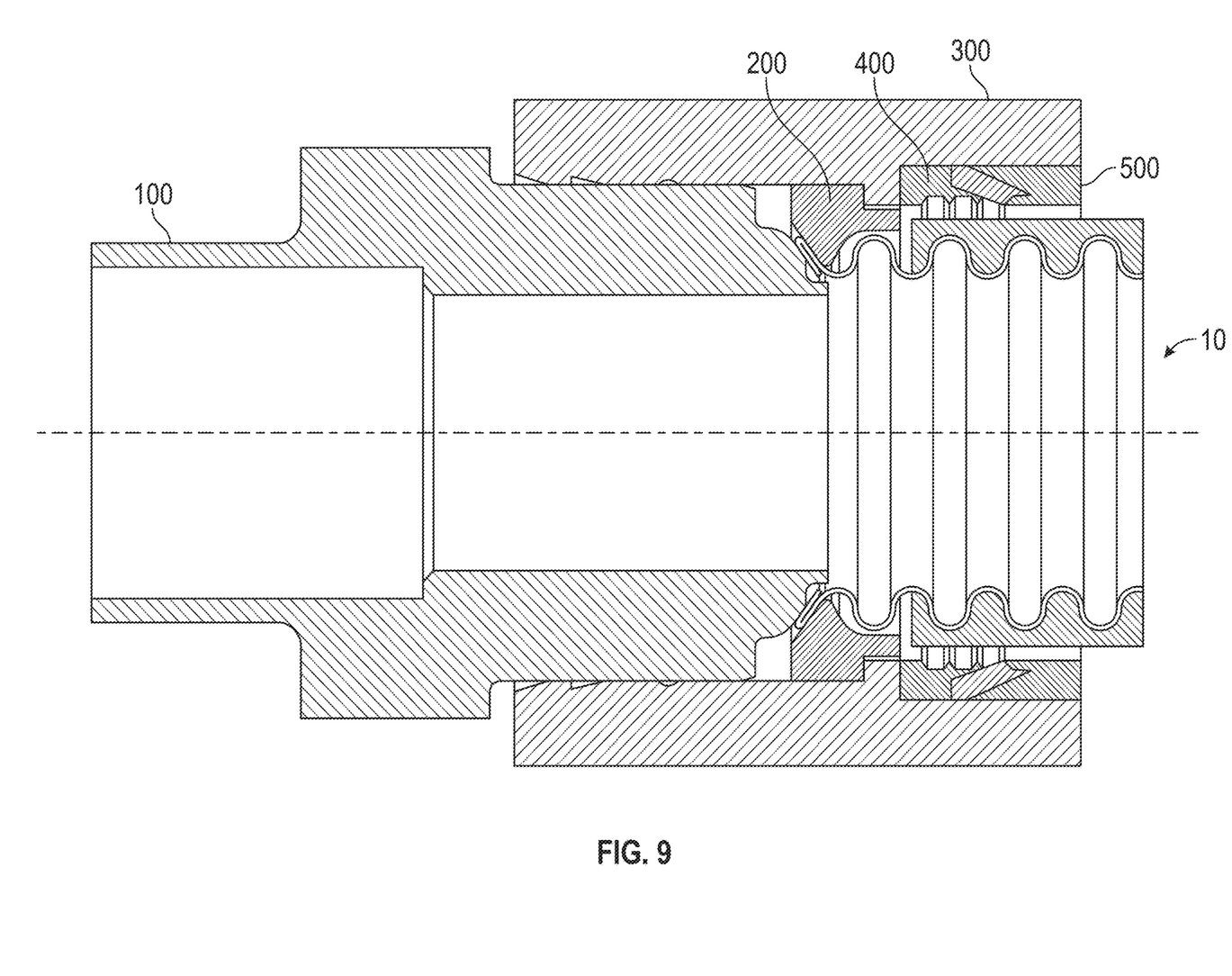
FIG. 9 is a cross-sectional view of the fitting and piping assembled in an example embodiment.

The fitting includes an adaptor 100, sealing member 200, nut 300, jacket lock ring 400 and swage sleeve 500. Each of these elements is described herein, along with the assembly of the fitting as depicted in FIG. 9. The adaptor 100, sealing member 200, nut 300, jacket lock ring 400 and swage sleeve 500 may be made from metal (e.g., brass or stainless steel).

Figure 2:
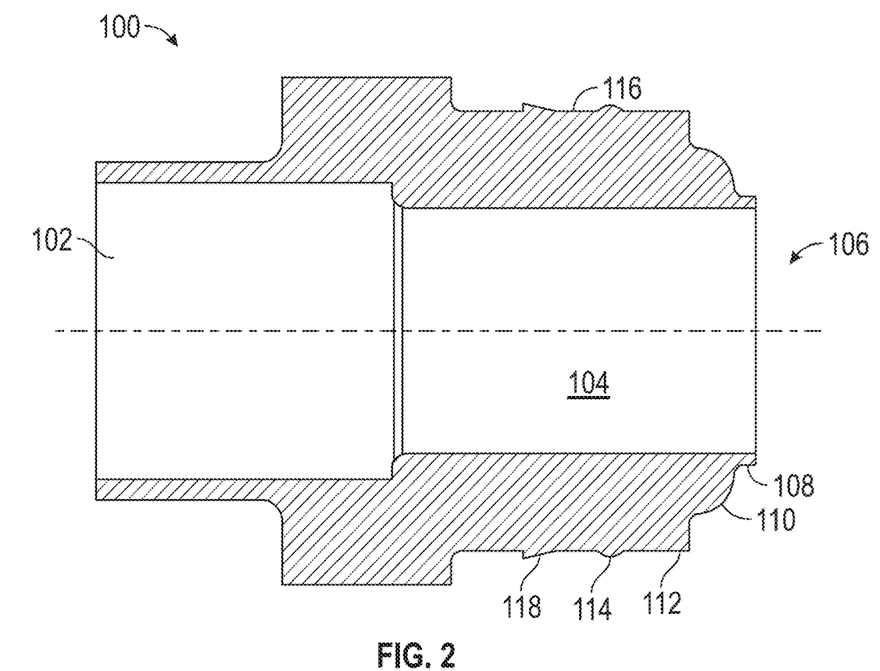
FIG. 2 is a cross-sectional view of an adaptor of FIG. 1.

FIG. 2 is a cross-sectional view of the adaptor 100. A first end of the adaptor 100 includes a cylindrical recess 102 for receiving a metal (e.g., copper) pipe. The metal pipe may be brazed to adaptor 100. Recess 102 may have various inner diameters to accommodate different sizes of metal pipe. A flow conduit 104 is formed in adaptor 100 centered about a centerline of the adaptor 100. At termination end 106 of the adaptor 100, a guiding diameter 108 is provided. The guiding diameter 108 is a cylindrical lip that is slightly smaller than the inner diameter of the metal tubing 12 (at a valley). The guiding diameter 108 facilitates centering the metal tubing 12 with the adaptor 100 to promote a better seal between the adaptor 100 and the metal tubing 12.

An adaptor sealing surface 110 is located adjacent to the guiding diameter 108. As described in further detail herein, the adaptor sealing surface 110 interacts with a sealing surface on sealing member 200 to compress the metal tubing 12 and form a metal-to-metal seal. In an embodiment, the adaptor sealing surface 110 is curved or arcuate. In an example embodiment, adaptor sealing surface 110 is a section of a sphere or toroid. The sealing surface on sealing member 200 may be linear, planar or frusto-conical. The interaction between the curved adaptor sealing surface 110 and the planar sealing surface on sealing member 200 creates a line seal, thereby reducing the axial compression load required to create a seal when installing the fitting.

Adjacent to the adaptor sealing surface 110 is an adaptor centering surface 112. The adapter centering surface 112 has an outer diameter slightly smaller than an inner diameter of a first cavity 306 (FIG. 3) of the nut 300 to center the nut 300 on the adaptor 100. A front edge of the adapter centering surface 112 may be chamfered to facilitate insertion of the adaptor 100 into the nut 300.

The adapter centering surface 112 adjoins a sealing ridge 114. The sealing ridge 114 has an outer diameter greater than the outer diameter of the adapter centering surface 112. The sealing ridge 114 has an outer diameter greater than the inner diameter of the first cavity 306 of the nut 300. The sealing ridge 114 may be curved and comprise a section of a sphere or toroid. As the outer diameter of the sealing ridge 114 has an outer diameter greater than the inner diameter of cavity 306 of the nut 300, the adaptor 100 is press fit into the nut 300 and creates a fluid impermeable seal between the adaptor 100 and nut 300.

An engagement surface 116 is located rearward of the sealing ridge 114. The engagement surface 116 has an outer diameter slightly smaller than a major diameter of the sealing ridge 114 and slightly larger than outer diameter of the adapter centering surface 112. The engagement surface 116 has an outer diameter slightly larger than the inner diameter of cavity 306 of the nut 300. The engagement surface 116 helps to center the adaptor 100 to the nut 300 as the adaptor 100 is press fit into the nut 300 and creates a snug fit between the adaptor 100 and nut 300.

A locking ridge 118 is located rearward of the engagement surface 116. The locking ridge 118 is slightly larger in major diameter than major diameter of sealing ridge 114 and larger than the inner diameter of cavity 306 of nut 300. The locking ridge 118 may be triangular is cross section, providing an edge that mechanically fixes the nut 300 on adaptor 100.

Figure 3:
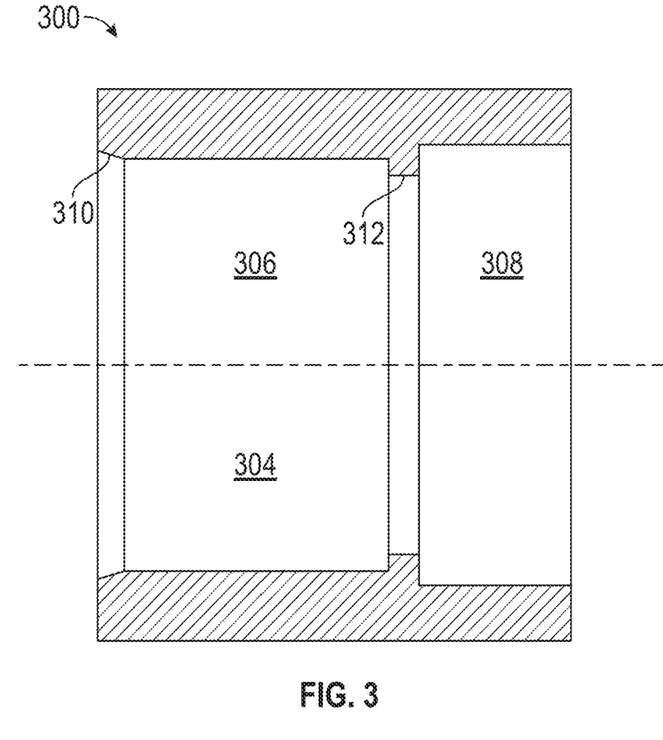
FIG. 3 is a cross-sectional view of a nut of FIG. 1.

FIG. 3 is a cross-sectional view of the nut 300 of FIG. 1. A flow conduit 304 is formed in nut 300 centered about a centerline of the nut 300. Nut 300 receives adaptor 100 in a first cavity 306 and receives the piping 10 through a second cavity 308. The first cavity 306 has a beveled opening 310 to facilitate insertion of the adaptor 100 into the first cavity 306. A shoulder 312 extends radially inwardly between the first cavity 306 and the second cavity 308 and serves as stop to limit travel of the sealing member 200.

Figure 4:
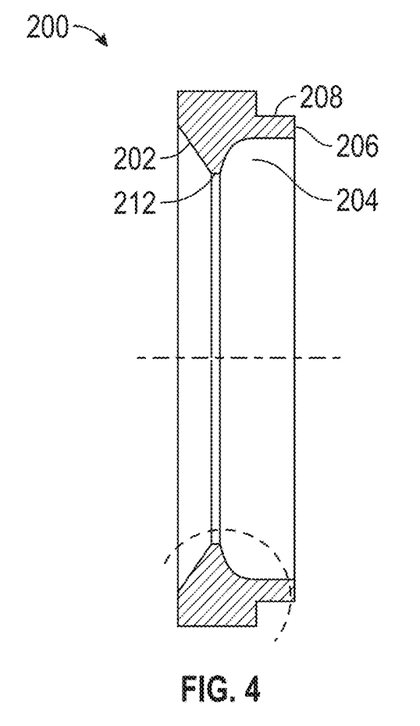
FIG. 4 is a cross-sectional view of a sealing member of FIG. 1.

FIG. 4 is a cross-sectional view of the sealing member 200 of FIG. 1. The sealing member may be implemented using a pair of split rings, a collet, a c-ring, etc. In FIG. 4, the sealing member 200 is a split ring. A forward end of the sealing member 200 (the end facing the adaptor 100) includes a sealing surface 202. In the example in FIG. 4, the sealing surface is linear in cross-section and may be frusto-conical. In an exemplary embodiment, the sealing surface 202 is 55 degrees relative to the central axis of the adaptor 100. It is understood that the sealing surface 202 may have different shapes. The rear end of the sealing member 200 (the end facing the piping 10) includes a cavity 204 having an arcuate shape to receive a peak of the metal tubing 12. A circumferential flange 206 extends rearward and defines a circumferential notch 208 on a periphery of the sealing member 200. The flange 206 has an outer diameter less than the inner diameter of shoulder 312 of the nut 300. Shoulder 312 is received in notch 208 when the fitting is assembled to limit travel of the sealing member 200, and therefore limit travel of piping 10.

The sealing member 200 includes a radially inward facing, circumferential lip 212. The inner diameter of the lip 212 is sized to be slightly larger than the outer diameter of a valley on the metal tubing 12. The lip 212 is received in a valley on the metal tubing 12 to position the sealing member 200 on the piping 10.

Figure 5:
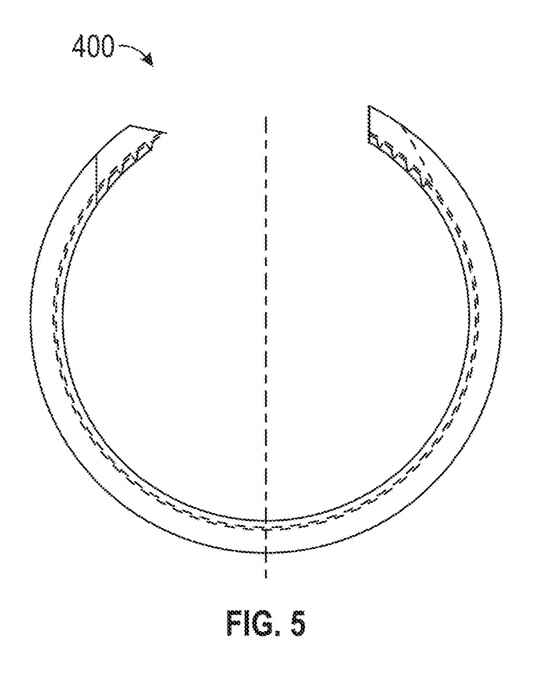
FIG. 5 is an end view of a jacket lock ring of FIG. 1.
Figure 6:
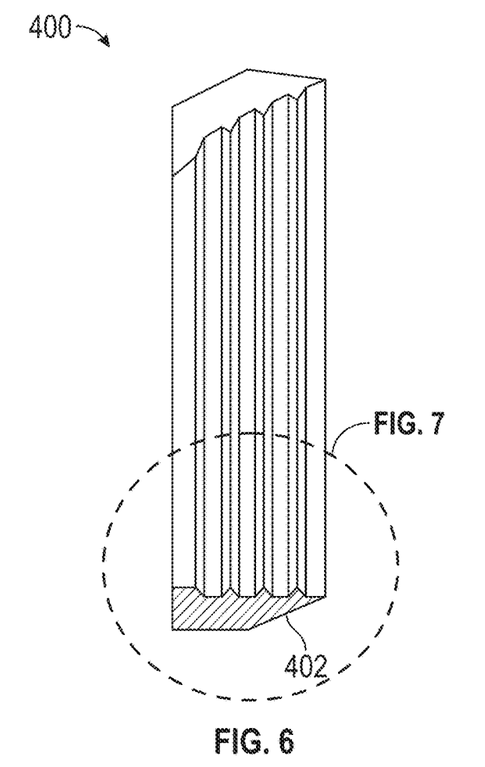
FIG. 6 is a partial cross-sectional view of the jacket lock ring of FIG. 1.
Figure 7:
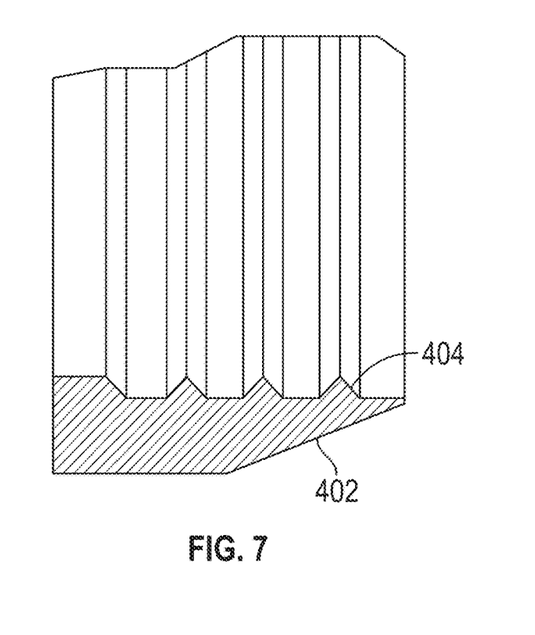
FIG. 7 is an exploded view of the jacket lock ring of FIG. 6.

FIG. 5 is an end view of a jacket lock ring 400 of FIG. 1. The jacket lock ring 400 in FIG. 5 is a C-ring that is compressed by the swage sleeve 500 to mechanically engage jacket 14 of piping 10. As shown in FIG. 6, the jacket lock ring 400 has a thickness x at a front end (facing the adaptor 100). The thickness of the jacket lock ring 400 tapers to a thickness, y, by virtue of ramp 402. In one embodiment, x is 0.15 inches and y is 0.007 inches. The inside surface of the jacket lock ring 400 includes one or more ridges 404 shaped to engage jacket 14 of piping 10. The ridges 404 may be radially arranged on an interior surface of the jacket lock ring 400. The ridges in FIG. 7 have triangular cross-section providing an edge to engage the jacket 14. It is understood that other cross-sections may be used for the ridge(s) 404. The outer diameter of the jacket lock ring 400 is slightly less than the inner diameter of second cavity 308 in nut 300.

Figure 8:
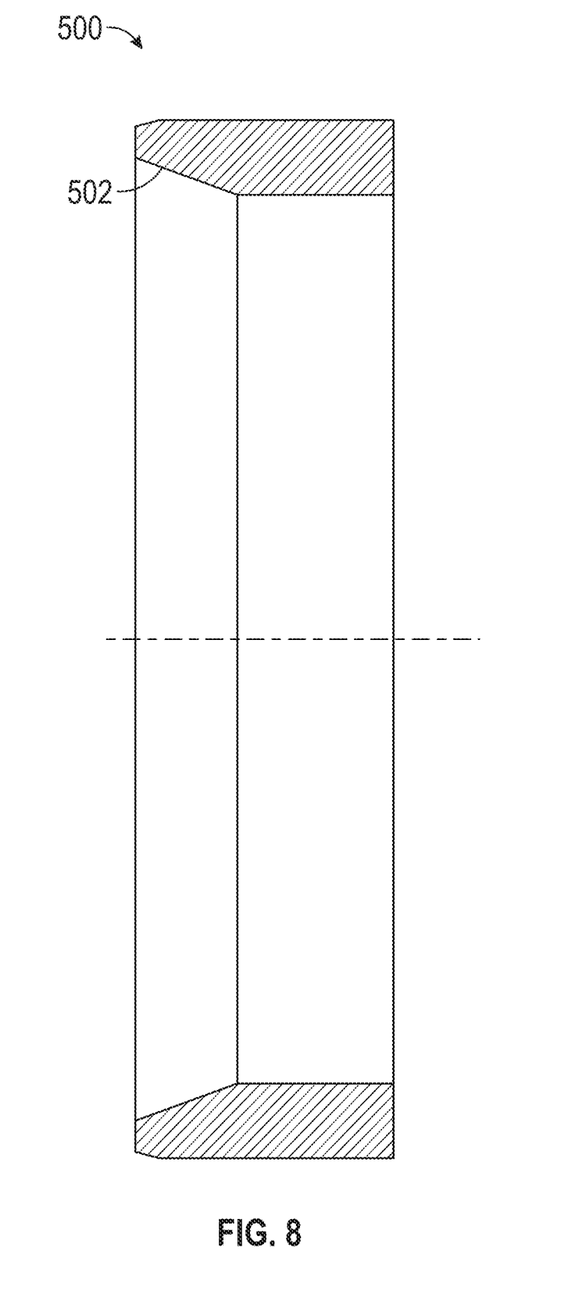
FIG. 8 is a cross-sectional view of a swage sleeve of FIG. 1.

FIG. 8 is a cross-sectional view of the swage sleeve 500 of FIG. 1. The swage sleeve 500 is generally cylindrical. A front edge (facing the adaptor 100) is angled (e.g., 20 degrees with respect to the centerline of the fitting) to define a tapered surface 502. The tapered surface 502 coacts with the ramp 402 on the jacket lock ring 400 to compress the jacket lock ring 400 inwards towards the centerline of the fitting. This drives the ridges 402 into jacket 14 to mechanically secure the fitting to the piping 10. The outer diameter of the swage sleeve 500 is slightly less than the inner diameter of second cavity 308 in nut 300 so that the swage sleeve 500 is press fit into the nut 300 to mechanically secure the swage sleeve 500 to the nut 300.

FIG. 9 is a cross-sectional view of the fitting and piping 10 assembled in an example embodiment. To assemble the fitting to the piping 10, the jacket 14 is removed to expose at least two full peaks and at least a portion of a valley past the second peak. The piping is cut at the distal end in a valley of the metal tubing 12.

The piping 10 is fed through the swage sleeve 500, jacket lock ring 400 and nut 300. The sealing device 200 is affixed to the exposed metal tubing 12 such that the sealing surface 202 is placed directly behind the first peak of the metal tubing 12, with lip 220 in a valley of the metal tubing 12. The piping 10 can then be pulled back until the sealing device 200 contacts shoulder 312 on nut 300. At this point the, jacket lock ring 400 and swage sleeve 500 can be positioned in second cavity 308 of nut 300, to the extent possible by hand. The adaptor 100 is positioned into first cavity 306 of nut 300, to the extent possible by hand.

Once the fitting is assembled by hand, a compression tool is used to simultaneously drive the adaptor 100 into nut 300 and drive the swage sleeve 500 into nut 300. Driving the adaptor 100 into first cavity 306 causes several actions to occur. A seal is formed between the adaptor sealing surface 110, the metal tubing 12 and the sealing surface 202. This seal is a primary seal, and comprises a double flare of metal tubing 12 compressed between the adaptor sealing surface 110 and the sealing surface 202. In embodiments where the adaptor sealing surface 110 is arcuate, a line seal is formed on the metal tubing 12.

The sealing ridge 114 engages the inner diameter of cavity 306 of the nut 300, to create a fluid impermeable seal between the adaptor 100 and nut 300. The locking ridge 118 engages the inner surface of cavity 306 of nut 300, to mechanically fix the nut 300 to adaptor 100. The swage sleeve 500 is driven into the second cavity 308 of the nut 300. The tapered surface 502 coacts with the ramp 402 on the jacket lock ring 400 to compress the jacket lock ring 400 inwards towards the centerline of the fitting. This drives the ridges 402 into jacket 14 to mechanically secure the fitting to the piping 10, preventing any expansion under pressure. The interference between the outer diameter of the swage sleeve 500 and the inner diameter of the cavity 308 secures the swage sleeve 500 to the nut 300.

In embodiments, the piping may be installed in lengths far longer than that available with rigid, copper piping. This greatly reduces installation time by eliminating the need to set up and breakdown sealed, vented installation areas. Further, using a press-fit connection eliminates the need for brazing the fitting to the piping.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A fitting for use with metal, corrugated tubing having peaks and valleys, the fitting comprising:
a nut configured to receive the tubing;
a sealing member for placement in a valley of the tubing, the sealing member including a sealing surface; and
an adaptor including an adaptor sealing surface;
wherein upon assembly, the adaptor is press fit into the nut and the tubing is compressed between the adaptor sealing surface and the sealing surface;
wherein the nut includes a first cavity configured to receive the adaptor;
the adaptor including a sealing ridge formed thereon, the sealing ridge having an outer diameter greater than an inner diameter of the first cavity, the adaptor being press fit into the nut.

2. The fitting of claim 1, wherein the adaptor sealing surface is arcuate.

3. The fitting of claim 2, wherein the adaptor sealing surface is spherical or toroidal.

4. The fitting of claim 2, wherein the sealing surface is flat.

5. The fitting of claim 2, wherein the sealing surface is frusto-conical.

6. The fitting of claim 1, wherein the nut includes a first cavity configured to receive the adaptor;
the adaptor including a locking ridge formed thereon, the locking ridge having an outer diameter greater than an inner diameter of the first cavity.

7. The fitting of claim 6, wherein the locking ridge includes an edge that mechanically fixes the nut on adaptor.

8. The fitting of claim 1, wherein:
the adapter includes a locking ridge formed thereon and spaced from the sealing ridge, the locking ridge having an outer diameter greater than the outer diameter of the sealing ridge.

9. The fitting of claim 8, wherein the locking ridge includes an edge that mechanically fixes the nut on adaptor.

10. The fitting of claim 8, wherein the adaptor includes an engagement surface located between the sealing ridge and the locking ridge, the engagement surface having an outer diameter greater than the inner diameter of the first cavity.

11. The fitting of claim 1, wherein:
the nut includes a second cavity; and
the tubing includes a jacket;
the fitting further comprising:
a jacket lock ring configured for placement in the second cavity, the jacket lock ring including an outer surface including a tapered ramp and an inner surface including at least one ridge configured to engage the jacket;
a swage sleeve configured for placement in the second cavity, the swage sleeve including a tapered surface facing the ramp on the jacket lock ring.

12. The fitting of claim 11, wherein:
wherein upon assembly, the swage sleeve is press fit into the second cavity and the tapered surface of the swage sleeve engages the ramp of the jacket lock ring to drive the jacket lock ring towards the jacket.

13. A fitting for use with metal, corrugated tubing having peaks and valleys encased in a jacket, the fitting comprising:
a nut including a first cavity and a second cavity and a shoulder extending radially inwardly between the first cavity and the second cavity, configured to receive the tubing through the second cavity;
a sealing member configured for placement in a valley of the tubing, the sealing member including a sealing surface and a circumferential notch, the notch configured to abut against and receive the shoulder to limit movement of the sealing member;
an adaptor including an adaptor sealing surface, the adaptor including a sealing ridge formed thereon, the sealing ridge having an outer diameter greater than an inner diameter of the first cavity, the adaptor being press fit into the nut by engagement between the sealing ridge and the inner diameter of the first cavity;
a jacket lock ring configured for placement in the second cavity, the jacket lock ring including an outer surface including a tapered ramp and an inner surface including at least one ridge configured to engage the jacket;
a swage sleeve configured for placement in the second cavity, the swage sleeve including a tapered surface facing the ramp on the jacket lock ring;
wherein upon assembly, the adaptor is press fit into the first cavity and the swage sleeve is press fit into the second cavity, the tubing being compressed between the adaptor sealing surface and the sealing surface and the tapered surface of the swage sleeve engages the ramp of the jacket lock ring to drive the jacket lock ring towards the jacket.

* * * * *